(12) United States Patent
MeReddy et al.

(10) Patent No.: US 8,263,810 B2
(45) Date of Patent: Sep. 11, 2012

(54) STABLE BORANE REAGENTS AND METHODS FOR THEIR USE

(75) Inventors: Venkatram R. MeReddy, Duluth, MN (US); Kanth V. B. Josyula, Germantown, WI (US)

(73) Assignees: Regents of the University of Minnesota, St. Paul, MN (US); Sigma-Aldrich Co. LLC, St. Louis, MO (US)

( * ) Notice: Subject to any disclaimer, the term of this patent is extended or adjusted under 35 U.S.C. 154(b) by 1108 days.

(21) Appl. No.: 12/123,307

(22) Filed: May 19, 2008

(65) Prior Publication Data

US 2008/0287708 A1 Nov. 20, 2008

Related U.S. Application Data

(60) Provisional application No. 60/938,528, filed on May 17, 2007.

(51) Int. Cl.
*C07F 5/02* (2006.01)
(52) U.S. Cl. .......................................................... 568/1
(58) Field of Classification Search ........................ 568/1
See application file for complete search history.

(56) References Cited

U.S. PATENT DOCUMENTS 6,118,026 A * 9/2000 Mitsui et al. ...................... 568/6

FOREIGN PATENT DOCUMENTS

WO WO 2006/020639 2/2006

OTHER PUBLICATIONS

Brown, "Asymmetric Carbon-Carbon Bond Formation via β-Allyldiisopinocampheylborane. Simple Synthesis of Secondary Homoallylic Alcohols with Excellent Enantiomeric Purities", *J. Am. Chem. Soc.*, 105, 2092-2093, 1983.

Brown, "Enantiomeric (Z)- and (E)-Crotyldiisopinocampheylboranes. Synthesis in High Optical Purity of All Four Possible Stereoisomers of B-Methylhomoallyl Alcohols", *J. Am. Chem. Soc.*, 108, 293-294, 1986.

Brown, "Chiral Synthesis via Organoboranes. 7. Diastereoselective and Enantioselective Synthesis of *erythro*- and *threo*-βMethylhomoallyl Alcohols via Enantiomeric (Z)- and (E)-Crotylboranes", *J. Am. Chem. Soc.*, 108, 5919-5923, 1986.

Brown, "Chiral Synthesis via Organoboranes. 13. A Highly Diastereoselective and Enantioselective Addition of [(Z)-γ-Alkoxyallyl]diisopinocampheylboranes to Aldehydes", *J. Am. Chem. Soc.*, 110, 1535-1538, 1988.

Josyula, "Exceptionally Facile Asymmetric Allylboration of Aldehydes in Water with IPC2Bally1 at High Temperatures", Abstract No. 85, American Chemical Society, Western Regional Meeting, 2007, 1 page.

Josyula, "Enabling boron-based reagents in chemical synthesis: A story of advancing science through new product development at Aldrich", Paper No. 58, American Chemical Society National Meeting, Young Industrial Investigators Symposium, 2008, 1 page.

Mereddy, "Stability Studies and the Development of Higher Temperature Allylation Utilizing (+) and (−) B-Allyldiisopinocampheylboranes", Abstract No. 123, American Chemical Society, Great Lakes Regional Meeting, 2006.

Ramachandran, "Stereoselective Synthesis of (+)-Goniodiol, (−)-8-Epigoniodio, and (+)-9-Deoxygoniopypyrone via Alkoxyallylboration and Ring-Closing Metathesis", *J. Org. Chem.*, 67, 7547-7550, 2002.

Ramachandran, "Diastereoselective Dihydroxylation and Regioselective Deoxygenation of Dihydropyranones: A Novel Protocol for the Stereoselective Synthesis of $C_1$-$C_8$ and $C_{15}$-$C_{21}$ Subunits of (+)-Discodermolide", *J. Org. Chem.*, 69, 6294-6304, 2004.

Ramachandran, "Studies towards the synthesis of epothilone A via organoboranes", *Org. Biolmol. Chem.*, 3, 3812-3824, 2005.

* cited by examiner

*Primary Examiner* — Peter G O Sullivan
(74) *Attorney, Agent, or Firm* — Viksnins Harris & Padys PLLP

(57) ABSTRACT

The invention provides methods for storing boranes (e.g. B-allyldiisopinocampheylborane). The invention also provides stable compositions comprising boranes, as well as methods for carrying out allylboration at high temperature and/or in the presence of water.

18 Claims, No Drawings

STABLE BORANE REAGENTS AND METHODS FOR THEIR USE

REFERENCE TO RELATED APPLICATIONS

This application claims priority under 35 U.S.C. 119(e) from U.S. Provisional Application Ser. No. 60/938,528 filed May 17, 2007, which is incorporated herein by reference.

BACKGROUND OF THE INVENTION

Allylation is one of the extremely important C—C bond forming reactions. Accordingly several "allyl" metal species have been extensively employed in the reaction with functional groups such as carbonyl (C=O) and imine (C=N), leading to the formation of the corresponding homoallylic alcohols or amines respectively. Among the several metals employed for allylation, allylboranes are highly unique and proceed with high stereoselectivity. The diastereoselectivity arises via a rigid six-membered chair like transition state due to the similarities in size of boron and carbon.

There have been significant advances made in the development of enantioselective versions of allylboration utilizing chiral allylboranes derived from α-pinene, tartarate, camphor etc. Of the several chiral auxiliaries employed, α-pinene is of special importance as the corresponding allylboranes result in very high enantiomeric excesses (ee) for a wide variety of aldehydes and imines (Scheme 1). See Brown, H. C.; Jadhav, P. K. *J. Am. Chem. Soc.* 1983, 105, 2092; Brown, H. C.; Bhat, K. S. *J. Am. Chem. Soc.* 1986, 108, 293; Brown, H. C.; Bhat, K. S. *J. Am. Chem. Soc.* 1986, 108, 5919; Brown, H. C.; Jadhav, P. K.; Bhat, K. S. *J. Am. Chem. Soc.* 1988, 110, 1535; Ramachandran, P. V., et al., *Org. Biomol. Chem.* 2005, 3, 3812; Ramachandran, P. V., et al., *J. Org. Chem.* 2004, 69, 6294; and Ramachandran, P. V., et al., *J. Org. Chem.* 2002, 67, 7547.

Scheme 1: Reaction of allylboranes with carbonyls and imines

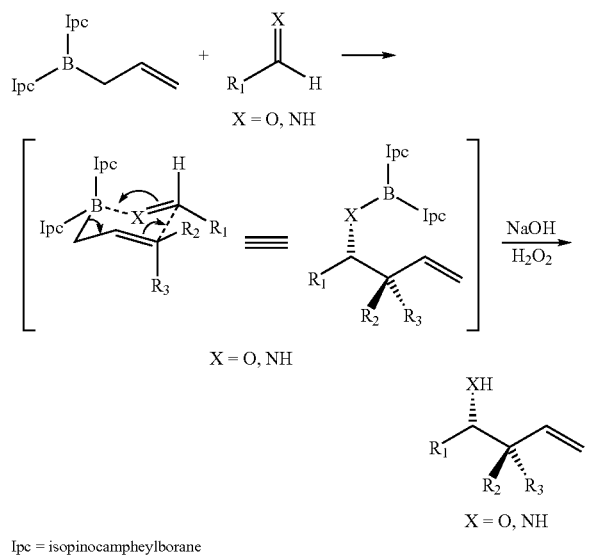

Ipc = isopinocampheylborane

The reaction with α-pinene derived boranes is reagent controlled, and the ee of the product obtained depends on the antipode of α-pinene used, regardless of the chirality in the substrate. One such α-pinene reagent is B-allyldiisopinocampheylborane, which provides exceptional enantioselectivity for aldehydes and imines at low temperatures. Unfortunately, B-allyldiisopinocampheylborane is not commercially available, due to its perceived instability. Thus, it is typically generated in situ or freshly prepared before use as illustrated in Scheme 2.

Scheme 2: Preparation of Ipc$_2$BAllyl Reagent

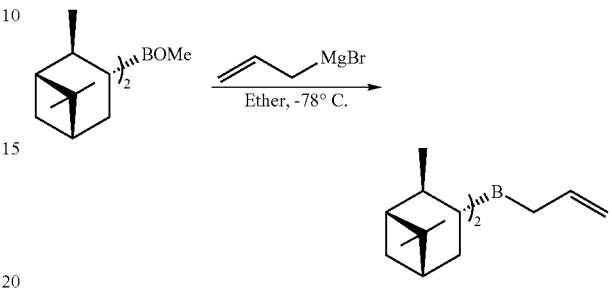

The preparation is tedious and involves the reaction of B-methoxydiisopinocampheylborane with allylmagnesium bromide in ether at 0° C. using Brown's procedure ($^{11}$B NMR shows a peak at ~78 PPM). The reaction generates a large amount of solid methoxymagnesium bromide that needs to be filtered under inert atmosphere, followed by repeated washings with pentane to precipitate the excess Grignard reagent. The reagent thus obtained is typically used for allylboration reactions as a 1-2M solution in pentane at low temperatures (−78° C. to −100° C.).

In view of the versatility of this reagent and its enormous potential for application in pharmaceutical industry, there is a need for a stabilized form of B-allyldiisopinocampheylborane as well as other borane reagents that can be stored and sold commercially. There is also a need for improved methods for using such reagents that require less stringent handling requirements.

SUMMARY OF THE INVENTION

The invention provides stable forms of boranes (e.g. B-allyldiisopinocampheylborane) that can be stored, shipped, and used on commercial scale. The invention also provides methods for performing allylboration at increased temperatures and in the presence of water. Such methods reduce the need for low temperatures and inert atmospheres, making the reagent more attractive for use on a commercial scale.

Accordingly in one embodiment, the invention provides a method comprising storing a borane of formula (I):

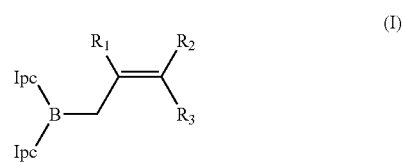

(I)

wherein $R_1$, $R_2$, and $R_3$ are each independently selected from H, ($C_1$-$C_6$)alkyl, ($C_1$-$C_6$)alkoxy, aryl, and aryl($C_1$-$C_6$)alkyl; and each Ipc is isopinocampheyl; under conditions such that less than 10% of the borane by weight decomposes after three days.

In another embodiment the invention provides a method comprising treating a compound comprising a carbonyl group or an imine group with a borane of formula (I) that is at least 3 days old:

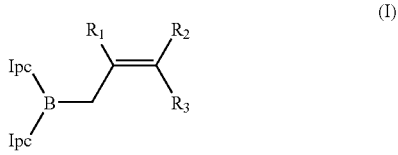

wherein $R_1$, $R_2$, and $R_3$ are each independently selected from H, $(C_1-C_6)$alkyl, $(C_1-C_6)$alkoxy, aryl, and aryl$(C_1-C_6)$alkyl; and each Ipc is isopinocampheyl.

In another embodiment the invention provides a composition comprising dioxane and a borane of formula (I):

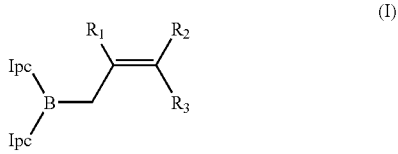

wherein $R_1$, $R_2$, and $R_3$ are each independently selected from H, $(C_1-C_6)$alkyl, $(C_1-C_6)$alkoxy, aryl, and aryl$(C_1-C_6)$alkyl; and each Ipc is isopinocampheyl.

In another embodiment the invention provides a kit comprising 1) packaging material, and 2) a borane of formula (I) that is at least 3 days old:

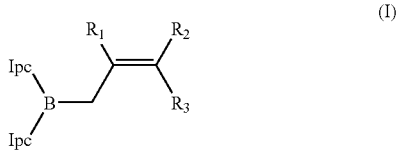

wherein $R_1$, $R_2$, and $R_3$ are each independently selected from H, $(C_1-C_6)$alkyl, $(C_1-C_6)$alkoxy, aryl, and aryl$(C_1-C_6)$alkyl; and each Ipc is isopinocampheyl.

In another embodiment the invention provides a method comprising reducing an organic compound with a borane in an aqueous solvent.

In another embodiment the invention provides a method for converting a first compound to a second compound comprising treating the first compound with a borane in an aqueous solvent to provide the second compound.

In another embodiment the invention provides a method comprising reducing an organic compound with a borane at a temperature of greater than or equal to −5° C.

In another embodiment the invention provides a method for converting a first compound to a second compound comprising treating the first compound with a borane at a temperature of greater than or equal to −5° C. to provide the second compound.

DETAILED DESCRIPTION

Applicant has determined that borane reagents such as B-allyldiisopinocampheylborane can be stored for months without any appreciable decomposition Additionally, allylboration of aldehydes was carried out with this reagent at ice-salt temperatures instead of −78° C. to −100° C. with only a slight decrease in the enantioselectivity. Remarkably, the reaction can be performed in water at high temperatures making this procedure environmentally benign and industrially attractive.

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic.

The term $(C_5-C_{12})$ hydrocarbon includes both straight and branched hydrocarbons having from five to twelve carbon atoms as well as mixtures thereof (e.g. pentanes, hexanes, heptanes, octanes, nonanes, decanes, etc.).

The term $(C_4-C_{10})$ ether includes straight and branched hydrocarbon ethers and aryl ethers having a total of four to ten carbon atoms, and mixtures thereof (e.g. diethylether, diisopropylether, dioxane, phenylmethylether, etc.).

The term halogenated $(C_1-C_{10})$ hydrocarbon includes both straight and branched hydrocarbons having from five to twelve carbon atoms that are substituted with one or more halo atoms, and mixtures thereof (e.g. dichloromethane, chloroform, trichloromethane, etc.).

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; and aryl can be phenyl, indenyl, or naphthyl.

A) Stability Studies

The B-allyldiisopinocampheylborane reagent was prepared on a 200 mmol scale. Aliquots of the reagent were taken in 20 mL volumetric flasks fitted with a stop cock and standard solutions (1M and 2M) were prepared in various solvents such as pentane, ether, $CH_2Cl_2$, and 1,4-dioxane (mp 12° C.), cyclohexane (mp 7° C.), cyclooctane (mp 12° C.) and benzene (mp 6° C.). Initially, 1M and 2M solutions were refrigerated at 4° C. after determining the purity based on $^{11}B$ NMR.

The stability of the reagent was evaluated periodically after every one month via $^{11}B$ NMR. No appreciable decomposition was observed after 4 months in solvents such as dioxane, benzene, and pentane. However, about 10-20% decomposition was observed in some other solvents tested (e.g. cyclohexane, cyclooctane, dichloromethane, and diethyl ether). Low melting solvents like dioxane and benzene at 4° C. are postulated to impart reagent stabilization due to restricted movement. The non-polar nature of the pentane solutions may assist in long term stabilization of the reagent.

In one embodiment the invention provides a method comprising storing a borane for 10, 30, or 60 days or more. In another embodiment, the borane is stored at or below about 10° C. In another embodiment, the a borane is stored at or below about 0° C. In another embodiment, the borane is stored at or below about −10° C. In another embodiment, the invention further provides selling the borane that has been stored.

In another embodiment, the invention provides a composition comprising dioxane and a borane at a concentration of from about 0.05M to about 5M. In another embodiment, the borane is present at a concentration of from about 0.5M to about 3M. In another embodiment, the composition is a solid. The compositions of the invention can conveniently be stored at a temperature of from about −78° C. to about 25° C. In one embodiment, the compositions of the invention can be stored at a temperature of from about −78° C. to about 25° C. In another embodiment, the compositions of the invention can be stored at a temperature of from about −78° C. to about 0° C.

In another embodiment, the invention provides a method for storing a borane comprising combining the borane and a solvent (e.g. dioxane, pentane, or a mixture thereof) to provide a composition, and storing the composition under conditions such that the concentration of the borane in the composition varies by less than about 10% by weight after three days. In another embodiment, the concentration of the borane in the composition varies by less than about 10% by weight after ten days. In another embodiment, the concentration of the borane in the composition varies by less than about 10% by weight after thirty days. In another embodiment, the concentration of the borane in the composition varies by less than about 5% by weight after three days. In another embodiment, the concentration of the borane in the composition varies by less than about 5% by weight after ten days. In another embodiment, the concentration of the borane in the composition varies by less than about 5% by weight after thirty days. In another embodiment, the concentration of the borane in the composition varies by less than about 1% by weight after three days. In another embodiment, the concentration of the borane in the composition varies by less than about 1% by weight after ten days. In another embodiment, the concentration of the borane in the composition varies by less than about 1% by weight after thirty days.

Typically, the compositions can be stored in an inert environment, e.g. under an inert gas such as argon or nitrogen, and/or in an air-tight vial or air-tight ampoule.

In another embodiment, the invention provides a kit comprising 1) packaging material, and 2) a solution comprising a borane that is at least 3 days old. In another embodiment, the borane in the kit is at least 10 days old. In another embodiment, the borane that is in the kit is at least 30 days old.

In one embodiment, the borane is a compound of formula (I).

In another embodiment, the borane is (β)-allyldiisopinocampheylborane.

B) High Temperature Allylboration

High temperature allylboration was performed using $Ipc_2Ballyl$ in pentane, dioxane and benzene on four different aldehydes (benzaldehyde, o-bromo-benzaldehyde, propionaldehyde and isobutylaldehyde). Before the addition of the aldehyde, the standard $IPC_2BAllyl$ reagents were diluted with 50% of pentane. Aldehydes were added at −15° C., the reactions were stirred at that temperature for 2 minutes, and oxidized under standard $NaOH$—$H_2O_2$ conditions. Work-up followed by purification afforded the corresponding homoallylic alcohols in good yield. The enantiomeric excesses were checked by comparing the specific rotation values with literature values and cross checked by chiral HPLC analysis using Chiralcel OD-H column with isopropanol-hexanes as eluting agent. Additionally, allylation of acetophenone provided 4-7% enantiomeric excess of the corresponding homoallylic alcohol at −15° C., which was identical to the value reported in the literature when the allylation was performed at −78° C.

In another embodiment, the invention provides a method comprising treating an organic compound with a borane at a temperature of greater than or equal to −5° C. In another embodiment, the organic compound is treated with a borane at a temperature of greater than or equal to 0° C. In another embodiment, the organic compound is treated with a borane at a temperature of less than or equal to about 10° C. In another embodiment, the organic compound comprises a carbonyl or an imine. In another embodiment, the compound is allylated with an ee of at least about 80%. In another embodiment, the compound is allylated with an ee of at least about 90%. In another embodiment, the compound is allylated with an ee of at least about 95%.

In one embodiment, the borane is a compound of formula (I).

In another embodiment, the borane is (β)-allyldiisopinocampheylborane.

C) Allylboration of Aldehydes with $IPC_2Ballyl$ in Water

Organic solvents are used extensively in the chemical industry, and their release into the environment has been a matter of great concern. A number of regulations are in place to govern solvents production, use, or disposal due to the wide range of hazards that are associated with these volatile organic compounds. Today, there is much emphasis on reduction of organic solvent usage and on using green chemistry.

Unexpectedly, exceptionally facile asymmetric allylboration of aldehydes with $IPC_2Ballyl$ was carried out in water at high temperatures. It is known that $IPC_2Ballyl$ is quenched in water. However, it has now been determined that $IPC_2Ballyl$ reacts with aldehydes faster than with water.

Thus, in another embodiment, the invention provides a method comprising treating an organic compound with a borane in an aqueous solvent. In another embodiment, the organic compound comprises a carbonyl or an imine. In another embodiment, the aqueous solvent comprises at least about 5% water by weight. In another embodiment, the aqueous solvent comprises at least about 10% water by weight. In another embodiment, the aqueous solvent comprises at least about 50% water by weight. In another embodiment, the aqueous solvent comprises at least about 75% water by weight. In another embodiment, the aqueous solvent is water.

In another embodiment, the invention provides a method comprising treating an organic compound with a borane under an atmosphere that comprises water. In another embodiment, the organic compound comprises a carbonyl or an imine. In another embodiment, the atmosphere comprises at least about 1% water by weight. In another embodiment, the atmosphere comprises at least about 10% water by weight. In another embodiment, the atmosphere comprises at least about 20% water by weight.

In one embodiment, the borane is a compound of formula (I).

In another embodiment, the borane is (β)-allyldiisopinocampheylborane.

The invention will now be illustrated by the following non-limiting Examples.

Example 1

Allylboration with B-allyldiisopinocampheylborane at High Temperature

Aldehyde (5.0 mmol) was added to a stirred solution of (+)-B-allyldiisopinocampheylborane ($Ipc_2BAllyl$) (7.0 mL, 1M solution) at −15° C. and maintained at that temperature for 2 minutes. The reaction was followed by $^{11}B$ NMR spectroscopy (δ56). Upon completion, the mixture was oxidized with 3.0 mL of 3.0 M NaOH and 3.0 mL of 30% $H_2O_2$, stirred for four hours at room temperature (about 22±3° C.) and extracted with $Et_2O$. The pure homoallylic alcohol was obtained upon silica gel column chromatography.

| Allylboration of aldehydes with standard IPC₂BAllyl reagents | | | |
|---|---|---|---|
| # | Aldehyde | Ipc₂BAllyl in Pentane (% ee) | Ipc₂BAllyl in Dioxane (% ee) |
| 1 | C₆H₅CHO | 94 | 92 |
| 2 | o-BrC₆H₄CHO | 92 | 90 |
| 3 | C₂H₅CHO | 92 | 90 |
| 4 | (CH₃)₂CHCHO | 90 | 89 |
| 5 | C₆H₅COCH₃ | 7 | 4 |

Example 2

Allylboration with B-allyldiisopinocampheylborane in Water as Solvent (+)-B-allyldiisopinocampheylborane (IPC₂BAllyl) (7.0 mL, 1M solution) was added to a stirred solution of aldehyde (5.0 mmol in 10 mL water) at 5° C. and maintained at that temperature for 2 minutes. The mixture was oxidized with 3.0 mL of 3.0 M NaOH and 3.0 mL of 30% H₂O₂, stirred for four hours at room temperature and extracted with Et₂O. The pure homoallylic alcohol was obtained upon silica gel column chromatography.

| # | Aldehyde | % ee | % yield |
|---|---|---|---|
| 1 | C₆H₅CHO | 90 | 91 |
| 2 | o-BrC₆H₄CHO | 89 | 92 |
| 3 | C₆H₁₁CHO | 85 | 88 |
| 4 | PhCH₂CHO | 86 | 89 |

Example 3

Preparation of B-allyldiisopinocampheylborane

To a flame dried 500 mL round bottomed flask cooled under an inert atmosphere, was added B-methoxydiisopinocampheylborane (15.82 g, 50 mol) under nitrogen and dissolved in 50 mL ether and cooled to −78° C. Allyl magnesium bromide (50 mL, 50 mmol) was added drop wise to the boronate solution and stirred for 1 hour. After the completion of the reaction as monitored by $^{11}$B NMR (δ79), the reaction mixture was filtered under nitrogen using Kramer's filter and was washed repeatedly with ether. The organic layer was concentrated under vacuum in nitrogen atmosphere. Spectroscopic grade pentane was added to it using a cannula, stirred for 5 minutes and allowed to settle down. The unreacted Grignard reagent and the magnesium salts get precipitated in pentane. The supernatant liquid was then transferred via a cannula into another round bottom flask under nitrogen and the solvent was evaporated off under vacuum. After repeated washing with pentane, the concentrate (>95%, 47.5 mmol) was dissolved in 47.5 mL pentane so as to prepare a 1 M stock solution of the reagent in pentane. Similarly stock solutions were prepared in different solvents such as dioxane, benzene, etc.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for stabilizing a borane comprising storing a borane of formula (I):

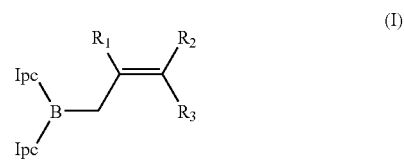

wherein $R_1$, $R_2$, and $R_3$ are each independently selected from H, $(C_1\text{-}C_6)$alkyl, $(C_1\text{-}C_6)$alkoxy, aryl, and aryl$(C_1\text{-}C_6)$alkyl; and each Ipc is isopinocampheyl; wherein the borane is stored in the presence of a solvent and the solvent comprises a $(C_5\text{-}C_{12})$ hydrocarbon, a $(C_4\text{-}C_{10})$ ether, or a halogenated $(C_1\text{-}C_{10})$ hydrocarbon, or a mixture thereof under conditions such that less than 10% of the borane by weight decomposes after three days.

2. The method of claim 1 wherein the borane is B-allyldiisopinocampheylborane.

3. The method of claim 1 wherein the solvent comprises pentane.

4. The method of claim 1 wherein the solvent comprises dioxane.

5. The method of claim 1 wherein less than about 5% of the borane by weight decomposes after thirty days.

6. The method of claim 1 wherein the borane is stored in an inert environment.

7. The method of claim 6 wherein the inert environment comprises argon or nitrogen gas.

8. The method of claim 6 wherein the borane is stored in an air-tight vial or air-tight ampoule.

9. The method of claim 1 wherein the borane is stored below room temperature.

10. The method of claim 1 wherein the borane is stored at room temperature.

11. A composition comprising dioxane and a borane of formula (I):

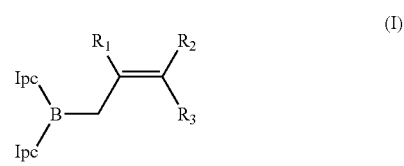

wherein $R_1$, $R_2$, and $R_3$ are each independently selected from H, $(C_1\text{-}C_6)$alkyl, $(C_1\text{-}C_6)$alkoxy, aryl, and aryl$(C_1\text{-}C_6)$alkyl; and each Ipc is isopinocampheyl.

12. The composition of claim 11 which is a solid.

13. A kit comprising 1) packaging material, and 2) a borane of formula (I) that is at least 3 days old:

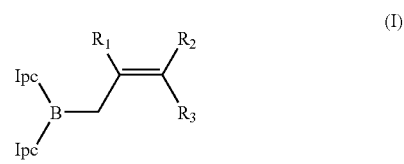

wherein $R_1$, $R_2$, and $R_3$ are each independently selected from H, $(C_1$-$C_6)$alkyl, $(C_1$-$C_6)$alkoxy, aryl, and aryl$(C_1$-$C_6)$alkyl; and each Ipc is isopinocampheyl wherein the borane is stored in the presence of a solvent and the solvent comprises a $(C_5$-$C_{12})$ hydrocarbon, a $(C_4$-$C_{10})$ ether, or a halogenated $(C_1$-$C_{10})$ hydrocarbon, or a mixture thereof.

14. The kit of claim 13 wherein the borane is stored in a solvent that comprises dioxane or pentane, or a mixture thereof.

15. The method of claim 1 wherein the solvent comprises benzene.

16. The kit of claim 13 wherein the borane is stored in a solvent that comprises benzene.

17. A composition comprising pentane and a borane of formula (I):

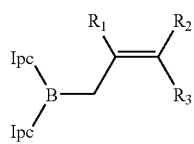

wherein $R_1$, $R_2$, and $R_3$ are each independently selected from H, $(C_1$-$C_6)$alkyl, $(C_1$-$C_6)$alkoxy, aryl, and aryl$(C_1$-$C_6)$alkyl; and each Ipc is isopinocampheyl.

18. A composition comprising a borane of formula (I):

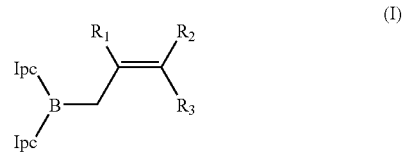

and further comprising a solvent wherein the solvent comprises a $(C_5$-$C_{12})$ hydrocarbon, a $(C_4$-$C_{10})$ ether, or a halogenated $(C_1$-$C_{10})$ hydrocarbon, or a mixture thereof wherein $R_1$, $R_2$, and $R_3$ are each independently selected from H, $(C_1$-$C_6)$alkyl, $(C_1$-$C_6)$alkoxy, aryl, and aryl$(C_1$-$C_6)$alkyl and each Ipc is isopinocampheyl.

* * * * *